US00PP11044P

United States Patent [19]

Meilland

[11] Patent Number: Plant 11,044

[45] Date of Patent: Aug. 31, 1999

[54] SHRUB ROSE PLANT NAMED 'MEIALATE'

[75] Inventor: Alain A. Meilland, Antibes, France

[73] Assignee: CP (Delaware), Inc., Wilmington, Del.

[21] Appl. No.: 09/031,833

[22] Filed: Feb. 27, 1998

[51] Int. Cl.[6] ..... A01H 5/00

[52] U.S. Cl. ..... Plt./102

[58] Field of Search ..... Plt./102, 104, 107, Plt./141, 143, 145, 148

*Primary Examiner*—Howard J. Locker

*Attorney, Agent, or Firm*—Burns, Doane, Swecker & Mathis, L.L.P.

[57] ABSTRACT

A new and distinct variety of shrub rose plant (i.e., garden rose plant) is provided which forms in abundance on a substantially continuous basis attractive semi-double blossoms that are Dresden Yellow suffused with Neyron Rose. The vegetation is vigorous and the growth habit is broad and bushy. Attractive medium green and semi-glossy foliage is formed. Good disease resistance is exhibited. Additionally, the new variety grows very well on its own roots following asexual reproduction by cuttings.

4 Drawing Sheets

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) of the new variety was the product of the cross between the 'Meineyta' variety (nonpatented in the United States) and the 'The Fairy' variety (nonpatented in the United States). The male parent (i.e., the pollen parent) of the new variety was the 'Meigronuri' variety (U.S. Plant Pat. No. 4,625). The parentage of the new variety can be summarized as follows:

('Meineyta'×'The Fairy')×'Meigronuri'.

The seeds resulting from the above pollination were sown and small plants were obtained which were physically and biologically different from each other. Selective study resulted in the identification of a single plant of the new variety.

It was found that the new variety of shrub rose plant of the present invention possesses the following combination of characteristics:

(a) abundantly and substantially continuously forms attractive semi-double blossoms that are Dresden Yellow suffused with Neyron Rose,
(b) exhibits a broad and bushy growth habit,
(c) forms vigorous vegetation,
(d) forms attractive medium green semi-glossy foliage,
(e) propagates well by cuttings, and
(f) exhibits good disease resistance.

The new variety well meets the needs of the horticultural industry. It can be grown to advantage as an attractive ornamentation in parks, gardens, public areas, and residential landscapes. Accordingly, it is particularly well suited for growing in the landscape.

The characteristics of the new variety have been found to be homogeneous and stable and are strictly transmissible by asexual propagation such as budding, grafting, and cuttage from one generation to another. The plant propagates well and grows very well on its own roots.

The new variety has been named the 'Meialate' variety.

BRIEF DESCRIPTION OF THE PHOTOGRAPHS

The accompanying photographs show, as nearly true as it is reasonably possible to make the same in color illustrations of this character, typical specimens of the plant and plant parts of the new variety. The rose plant specimens of the new variety illustrated herein were one year of age and were grown outdoors during December while budded on *Rosa froebelli* understock at LeCannet-des-Maures, Var, France except as otherwise indicated.

FIG. 1 illustrates typical blossoms and foliage of the new variety. The yellow blossoms suffused with red and the attractive semi-glossy foliage are shown. The darker red area visible on some petals was the result of cold damage in the Fall.

DETAILED DESCRIPTION

The chart used in the identification of colors is that of The Royal Horticultural Society (R.H.S. Colour Chart). The terminology which precedes reference to the chart has been added to indicate the corresponding color in more common terms. The description is based on one-year-old specimens of the new variety during September while budded on *Rosa froebelli* understock and grown outdoors at LeCannet-des-Maures, Var, France.

Class: Shrub (Garden Rose).

Plant:

*Height.*—Approximately 80 cm. on average at the end of the growing season.

*Width.*—Approximately 70 to 80 cm. on average at the end of the growing season.

Figure 4:
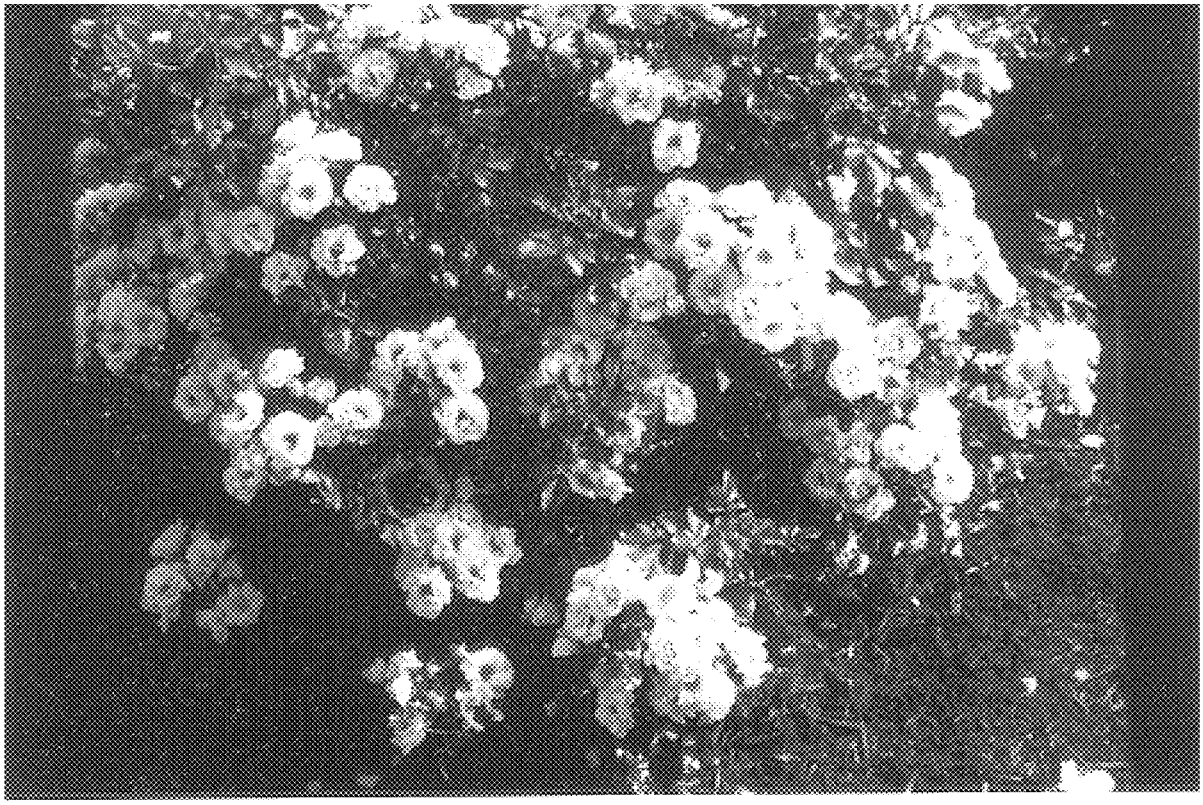
FIG. 4 illustrates the mounding growth habit of a two year-old plant of the new variety when grown in the landscape at West Grove, Pa. during June. The depicted blossom coloration appears to be lighter than that of FIG. 1 because of substantial fading to a creamy white coloration that commonly takes place during hot growing conditions.

*Habit.*—Broad and bushy. See the mounding shrub growth habit of FIG. 4. The height and width commonly are about equal.

Branches:

*Color.*—Young stems: light green, near Yellow-Green Group 146B. Adult wood: light green, near Yellow-Green Group 147C.

Figure 2:
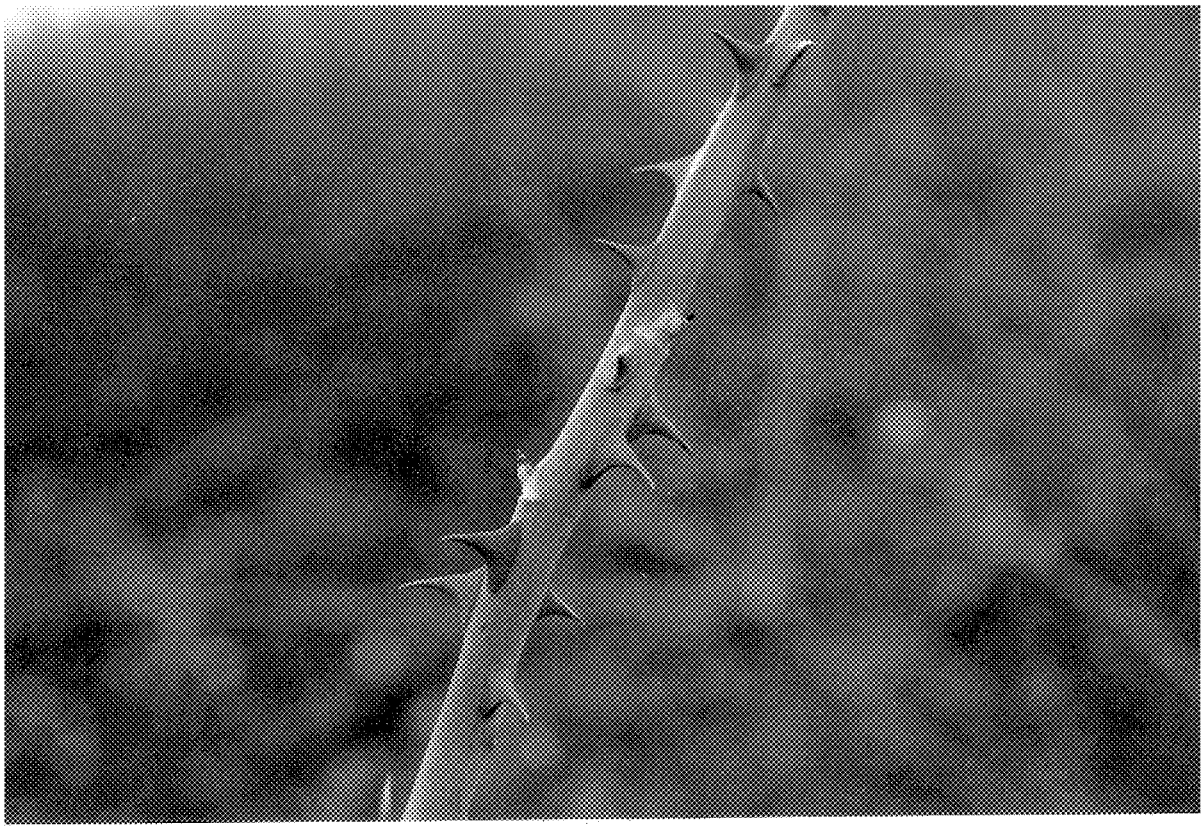
FIG. 2 illustrates a close-up view of a typical cane of the new variety wherein thorns and dormant buds are shown.

*Thorns.*—Size: Medium (as illustrated). Quantity: medium in number. Configuration: downwardly hooked as illustrated in FIG. 2. Color: brownish-red on young stems and on adult wood.

Leaves:

*Stipules.*—Adnate, pectinate, and rather large.

Figure 1:
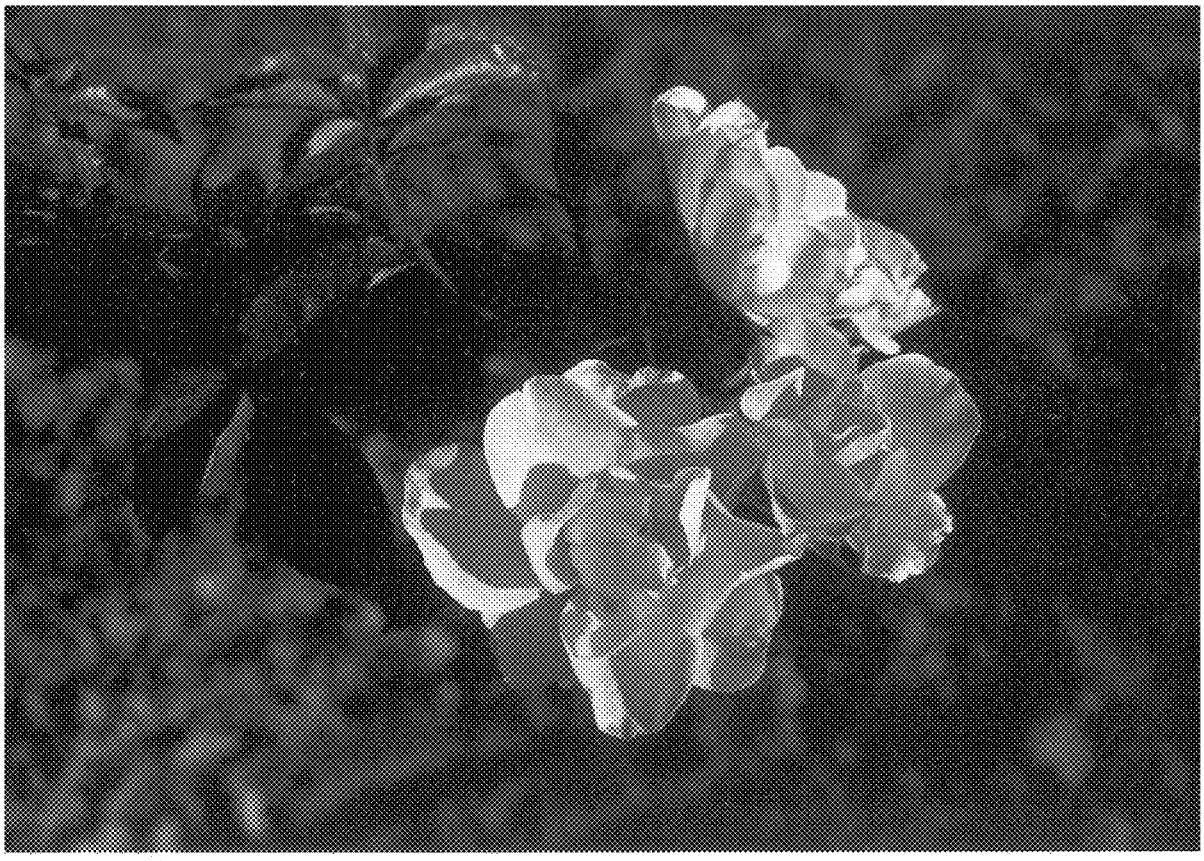

*Petioles.*—Upper surface: greenish during the growing season with the presence of a few glandular edges, and reddish in the Fall when FIG. 1 was obtained. Under surface: bear some prickles.

*Leaflets.*—Number: 3, 5, and 7 (most often). Shape: elliptic. Serration: serralate with apical spines as illustrated in FIG. 1. Texture: typical. Overall appearance: very dense, medium green in coloration, and semi-glossy. Color (young foliage): Upper surface: medium green, Yellow-Green Group 147B. Under surface: very light green, near Yellow-Green Group 147D. Color (adult foliage): Upper surface: dark green, Yellow-Green Group 147A. Under surface: medium green near Yellow-Green Group 147B.

Inflorescence:

*Number of flowers.*—Commonly approximately 6 to 15 blooms per floral stem.

*Peduncle.*—Short and rigid with some aciculae, reddish when young and greenish when mature, and approximately 1.5 to 2 cm. in length on average.

*Sepals.*—Upper surface: greenish in coloration (Greyed-Green Group 194A). Under surface: greenish in coloration (Greyed-Green Group 194A). Configuration: commonly without extensions.

*Buds.*—Shape: conical. Length: approximately 1.5 to 2 cm. on average. Size: medium. Color (when opening): Upper surface: near Dresden Yellow, Yellow Group 5A, and widely suffused with near Azalea Pink, Red Group 38A. Under surface: near Dresden Yellow, Yellow Group 5A, and widely suffused with near Azalea Pink, Red Group 38A.

*Flower.*—Form: cup-shaped, somewhat flattened, and semi-double. Diameter: approximately 5 to 6 cm. on average. Color (when opening begins): Upper surface: near Dresden Yellow, Yellow Group 5A, and widely suffused with near Azalea Pink, Red Group 38A. Under surface: near Dresden Yellow, Yellow Group 5A, and widely suffused with near Azalea Pink, Red Group 38A. Color (when blooming): Upper surface: near light Dresden Yellow, Yellow Group 5D, and lightly suffused with near Neyron Rose, Red Group 55C to 55D. Under surface: near light Dresden Yellow, Yellow Group 5D, and lightly suffused with Neyron Rose, Red Group 55C. Color (at end of blooming): Upper surface: near Dresden Yellow, Yellow Group 5D, and lightly suffused with very light Neyron Rose, Red Group 55D. Under surface: near Dresden Yellow, Yellow Group 5D, and lightly suffused with very light Neyron Rose, Red Group 55D. Fragrance: none. Petal form: rounded. Petal number: approximately 19 to 22 on average. Stamen number: approximately 66 on average. Anthers: yellow in coloration. Filaments: yellow in coloration. Pistils: approximately 34 on average. Stigmas: yellow in coloration. Styles: yellow in coloration. Receptacle: greenish in coloration, and in longitudinal section it is narrow and in the shape of a pitcher. Fruits: very abundant, fertile, medium in size, and near Red Group 44B in coloration.

Development:

*Vegetation.*—Strong.

*Blossoming.*—Very abundant and substantially continuous.

Figure 3:
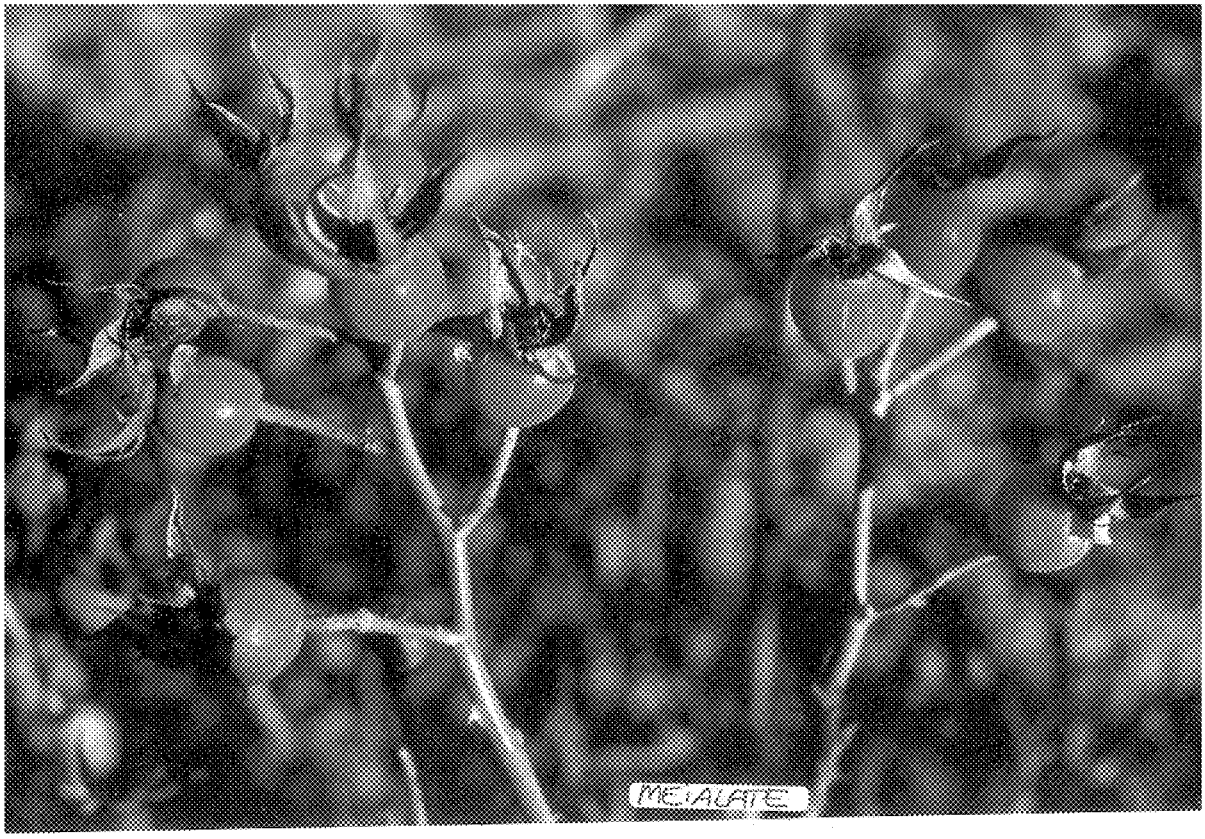
FIG. 3 illustrates typical bright red rose hips formed in abundance on the new variety.

*Aptitude to bear fruits.*—Very good, as illustrated in FIG. 3.

*Resistance to diseases.*—Good with respect to powdery mildew and blackspot.

I claim:

1. A new and distinct variety of shrub rose plant characterized by the following combination of characteristics:

(a) abundantly and substantially continuously forms attractive semi-double blossoms that are Dresden Yellow suffused with Neyron Rose,
(b) exhibits a broad and bushy growth habit,
(c) forms vigorous vegetation,
(d) forms attractive medium green semi-glossy foliage,
(e) propagates well by cuttings, and
(f) exhibits good disease resistance;

substantially as herein shown and described.

* * * * *